United States Patent
Sarcia et al.

(10) Patent No.: US 12,173,926 B1
(45) Date of Patent: Dec. 24, 2024

(54) ROOM DISINFECTION SYSTEMS COMPRISING CONCENTRATED LIGHT SOURCES

(71) Applicant: Framework Product Development LLC, Lakeside, CA (US)

(72) Inventors: Sam Rhea Sarcia, Lakeside, CA (US); Scott Brian Mahar, Poway, CA (US)

(73) Assignee: Framework Product Development LLC, Lakeside, CA (US)

( * ) Notice: Subject to any disclaimer, the term of this patent is extended or adjusted under 35 U.S.C. 154(b) by 665 days.

(21) Appl. No.: 17/472,539

(22) Filed: Sep. 10, 2021

Related U.S. Application Data (60) Provisional application No. 63/076,383, filed on Sep. 10, 2020.

(51) Int. Cl.
| | |
|---|---|
| *F24F 8/22* | (2021.01) |
| *A61L 9/20* | (2006.01) |
| *F21Y 115/10* | (2016.01) |
| *G01N 21/3504* | (2014.01) |
| *G05B 15/02* | (2006.01) |

(52) U.S. Cl.
CPC .................... *F24F 8/22* (2021.01); *A61L 9/20* (2013.01); *G01N 21/3504* (2013.01); *G05B 15/02* (2013.01); *F21Y 2115/10* (2016.08)

(58) Field of Classification Search
CPC ..... A61L 9/00; A61L 9/16; A61L 9/18; A61L 9/20; F24F 8/00; F24F 8/20; F24F 8/22; G01N 21/00; G01N 21/17; G01N 21/25; G01N 21/31; G01N 21/35; G01N 21/3504
See application file for complete search history.

(56) References Cited

U.S. PATENT DOCUMENTS

| | | | |
|---|---|---|---|
| 2,418,195 A | | 4/1947 | Rolf |
| 2,569,772 A | | 10/1950 | Olsen |
| 5,871,522 A | | 2/1999 | Sentilles |
| 6,120,262 A | * | 9/2000 | McDonough .......... H05B 47/19 |
| | | | 318/16 |
| 7,763,212 B2 | | 7/2010 | McEllen |
| 8,080,203 B2 | | 12/2011 | First et al. |
| 8,921,813 B2 | | 12/2014 | Palmer et al. |
| 9,358,313 B2 | * | 6/2016 | Deal .................... H05B 47/115 |
| 2009/0004046 A1 | | 1/2009 | McEllen |
| 2016/0097511 A1 | | 4/2016 | Catalano |
| 2019/0298869 A1 | * | 10/2019 | Poulsen .................. F21S 8/063 |

OTHER PUBLICATIONS

Kowalski, et al., "UVGI design basics for air and surface disinfection", Heating, piping, and air conditioning, 72, 2001, 100-110.
First, et al., "Fundamental factors affecting upper-room ultraviolet germicidal irradiation—Part II. Predicting effectiveness", Journal of Occupational and Environmental Hygiene, 4(5), 2007, 352-362.
First, et al., "Fundamental factors affecting upper-room ultraviolet germicidal irradiation—Part I. Experimental", Journal of Occupational and Environmental Hygiene, 4(5), 2007, 321-331.

* cited by examiner

*Primary Examiner* — Natasha E Young (57) ABSTRACT

An upper-air disinfection system is achieved with a plurality of upper air emitters powered by a DC voltage power bus including data conductors. An upper air emitter with one or more concentrated light sources, quartz lenses, and one or more reflectors.

20 Claims, 5 Drawing Sheets

ROOM DISINFECTION SYSTEMS COMPRISING CONCENTRATED LIGHT SOURCES

CROSS-REFERENCE TO RELATED APPLICATIONS

This application claims the benefit of U.S. Provisional Application Ser. No. 63/076,383, filed Sep. 10, 2020, the content of which is incorporated by reference herein in its entirety.

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

BACKGROUND

Upper-room ultra-violet-germicidal-irradiation (UVGI), also known as upper-air disinfection, has been disclosed as a means of air disinfection where lighting fixtures irradiate the air above room occupants. The disinfection light is contained to the upper room and relies on the exchange of air between the upper and lower room in order to treat the complete room volume.

Upper-air disinfection devices can be may be used to reduce the spread of viruses. In the case of many human-transmissible viruses, a viral load may spread through respiratory exhalation in the form of liquid droplets. When these droplets enter another person through a respiratory inhalation or other path, the virus can then infect that person.

Depending on the size of the respiratory droplet, the net effect of all the physical forces can be quite different. Inertia, surface tension, gravity, inter-molecular forces, and interaction with a surrounding media, may affect a droplet, but different forces will dominate others depending on the size of a droplet. For instance, a larger sized droplet of 100 μm may be affected more strongly by inertial and gravitational forces, and may fall to the ground quickly. A 5 um droplet by contrast may be more strongly impacted by surface tension and interaction with the surrounding medium such that it tends to stay in the air and move with air current and becomes what is referred to as aerosolized. Droplets that fall to the floor quickly are often referred to as respiratory droplets, whereas droplets that are of a size sufficient to become aerosolized are referred to as droplet nuclei. For a given viral outbreak, one transmission vector may be more prevalent than another, or they may be of similar importance.

Masks and physical barriers can also be utilized to reduce the spread of a virus from respiratory droplets.

SUMMARY

Until recently, most germicidal light sources have been low or medium pressure mercury lamps comprising of two filaments and a quartz bulb encasing mercury vapor. These lamps are well characterized and low cost, but come with a series of drawbacks. Particularly, the mercury vapor can be hazardous to health and the quartz bulb is susceptible to damage during handling. More importantly, the light emitted by said bulbs is emitted from all surfaces, in all directions. In an upper-air disinfection system, it is preferable to orient the germicidal light output from a fixture to be substantially horizontal. With a distributed light source such as a bulb, this is challenging because of the diversity of ray orientations and positions which in practice requires the use of a set of louvers to block all rays not exiting the light source horizontally. One approach utilizes a linear parabolic reflector which will reflect all light emanating from the focal point of the parabolic section to be horizontal. However, even in this configuration, the reflector may only be active over one half of the rays emanating from a bulb, and in practice such devices still utilize a louver set to filter light ray not substantially horizontal.

While light emitting diodes (LEDs) have been known for many decades, there has been limited progress in manufacturing LEDs capable of producing light in the germicidal wavelength range of 100 nm to 280 nm. Although samples were produced, they were generally of very low specific power, very low efficiency, or very low lifetime compared to visible light LEDs. However, recent advancements in semiconductor manufacturing have paved a path for the development of high performing LEDs particularly in the 250 nm to 280 nm wavelength over the next several years. Similarly, recent advancements in Krypton Chloride Excimer lamps promises the availability of cost-effective 222 nm lamps in the near future.

LED light sources are particularly advantageous because they may be powered by low voltage DC power sources as compared to the AC main-powered ballasts used in vapor lamps. Additionally, they promise smaller lamp form factors and a higher fundamental power efficiency and lifetime, whereas current vapor lamps are at their practical efficiency and lifetime limit.

Most importantly, LEDs and Krypton Chloride Excimer lamps promise a very small volumetric size which has far-reaching implications for the design of upper-air disinfection systems. A concentrated light source may be more easily manipulated in an optical system because the emitted rays are concentrated in a single location which enables a wider array of optic and reflector elements.

While optical designs are widely understood for manipulating the output of concentrated light sources like LEDs in lighting applications, an upper-air emitter is a unique application where the desired output of the emitter is a set of rays spread uniformly across a room, while being limited to a narrow vertical spread. As LED light sources capable of providing germicidal light become available and cost effective, a set of optical designs capable of producing such an output pattern are needed.

Another benefit of LED-based upper air emitters powered by low voltage DC electricity is the ability for a relatively low optical output power modules to be produced cost effectively. In traditional AC-power systems, the fundamental components needed have a minimum characteristic power at which they can be cost-effectively produced. Particularly, the mechanical infrastructure needed for a reflector design and louver set has driven the development of relatively high-powered emitters producing in excess of 1 W of optical power. In an upper-air disinfection system, the more uniform the irradiance of a given light field can be, the more efficiently it will treat a space. Being able to produce a higher number of lower powered emitters for a similar or lower cost per total optical power would enable a much higher efficiency system by virtue of reducing irradiance gradients and being less reliant on room mixing to treat all air within a space uniformly.

While DC-powered LED emitter topologies support such a distributed approach, it is preferred to produce optical systems that can be manufactured in high volume, simply, and with low individual part costs. Further, it is preferred to have a system by which multiple emitters may be integrated into a built environment without prohibitive costs. This burden may be alleviated using interconnection and mounting strategies that have low material costs and may be implemented safely by a wide range of technicians that can workwith DC that does not have the same safety hazards as AC wiring which requires a licensed electrician.

The field of the disclosed design are upper-air emitters based on concentrated light sources, as well as systems powered by DC power supplies with an innate digital infrastructure such as is associated with most LED devices.

Certain embodiments of the disclosed systems and methods are comprised of a series of upper-air emitters which are powered by a DC power bus. In some embodiments, a single power supply may connect to AC mains power and be capable of powering dozens of individual emitters using one or more DC power busses. Additionally, the interconnect may include one or more conductors dedicated to data communication which allows a single controller unit to communicate with the plurality of emitters it is connected to. This allows for a reduction in the number of individual devices that need to access a wireless communication network and further reduces system cost.

Additional features disclosed in some embodiments include the use of a novel reflector that may manipulate the output of a concentrated light source into the desired horizontal orientation with a relatively small reflector that may be cost effectively produced.

Another optical system design is disclosed in which a set of reflectors may work in congress with one or more lenses to achieve a desired beam pattern output cost effectively and simply. Additional embodiments include the integration of environmental sensors as well as air circulators, and other features which enable a better user experience.

BRIEF DESCRIPTION OF THE DRAWINGS

This disclosure will be readily understood by referring to the following detailed description in conjunction with the accompanying drawings, in which.

DETAILED DESCRIPTION

A description of the systems and methods consistent with embodiments of the present disclosure is provided below. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The particular wording and terminology used to describe a particular embodiment or combinations of embodiments is an example of one combination and should not be considered as limited of the scope of invention or possible combinations claimed in the invention. Words like "comprise" or "comprising" are used to described how features and steps are combined to illustrate the invention but do not preclude the inclusion of additional steps and features or alternate combinations of thereof. Terminology used here has an intended meaning of that familiar to someone who is familiar with the state of the art and in the case that terminology is ambiguous or incorrect, it should not limit the intended meaning.

The embodiments of the disclosure may be understood by reference to the drawings, wherein like parts may in some instances be designated by like numbers or descriptions. The components of the disclosed embodiments, as generally described and/or illustrated in the figures herein, could be arranged and designed in a wide variety of different configurations. Thus, the following description of the embodiments of the systems and methods of the disclosure is not intended to limit the scope of the disclosure, but is merely representative of possible embodiments of the disclosure. In addition, the steps of any method disclosed herein do not necessarily need to be executed in any specific order, or even sequentially, nor need the steps be executed only once, unless otherwise specified.

Figure 1:
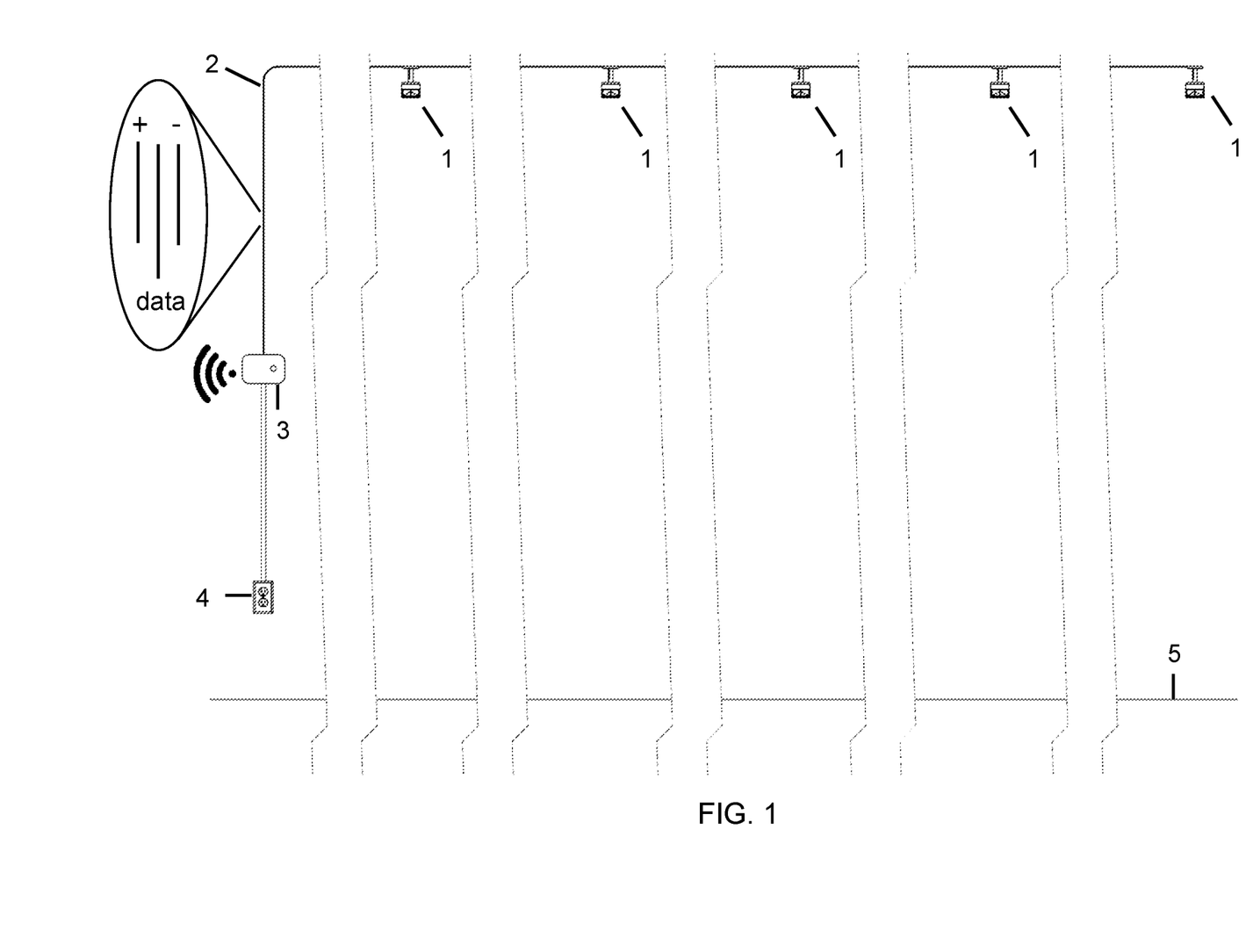
FIG. 1 shows a series of upper-air emitters powered by a single DC-voltage power bus, including a dedicated data line. A single controller unit connects to AC-mains power and contains a radio and processor capable of communicating with a wireless network.

A series of upper air emitters 1 are illustrated in in FIG. 1, each of which is powered by a DC power bus 2, including a dedicated data conductor. Said emitters are mounted at about 7 feet or above the room floor 5 so that the horizontally projected light is contained over the head of room occupants. Break lines are shown in the drawing to indicate that the space between the emitters is greater than that show in the drawing scale. Also shown is a control unit 3 which outputs the DC power bus with data conductor. This controller is capable of converting AC-mains power in DC power suitable for powering the upper-air emitters 1, and also capable of communicating with processors within each emitter over the data conductor. In some embodiments of the design there are two or more data conductors. Also, in some embodiments, the bottom surface of each emitter may be illuminated some visible color in order to indicate to room occupants that the upper-air emitter is active. In some embodiments, one or more emitters include environmental sensors, the output of which is reported to the control unit 3. The control unit 3 is wired to AC mains power 4.

Figure 2:
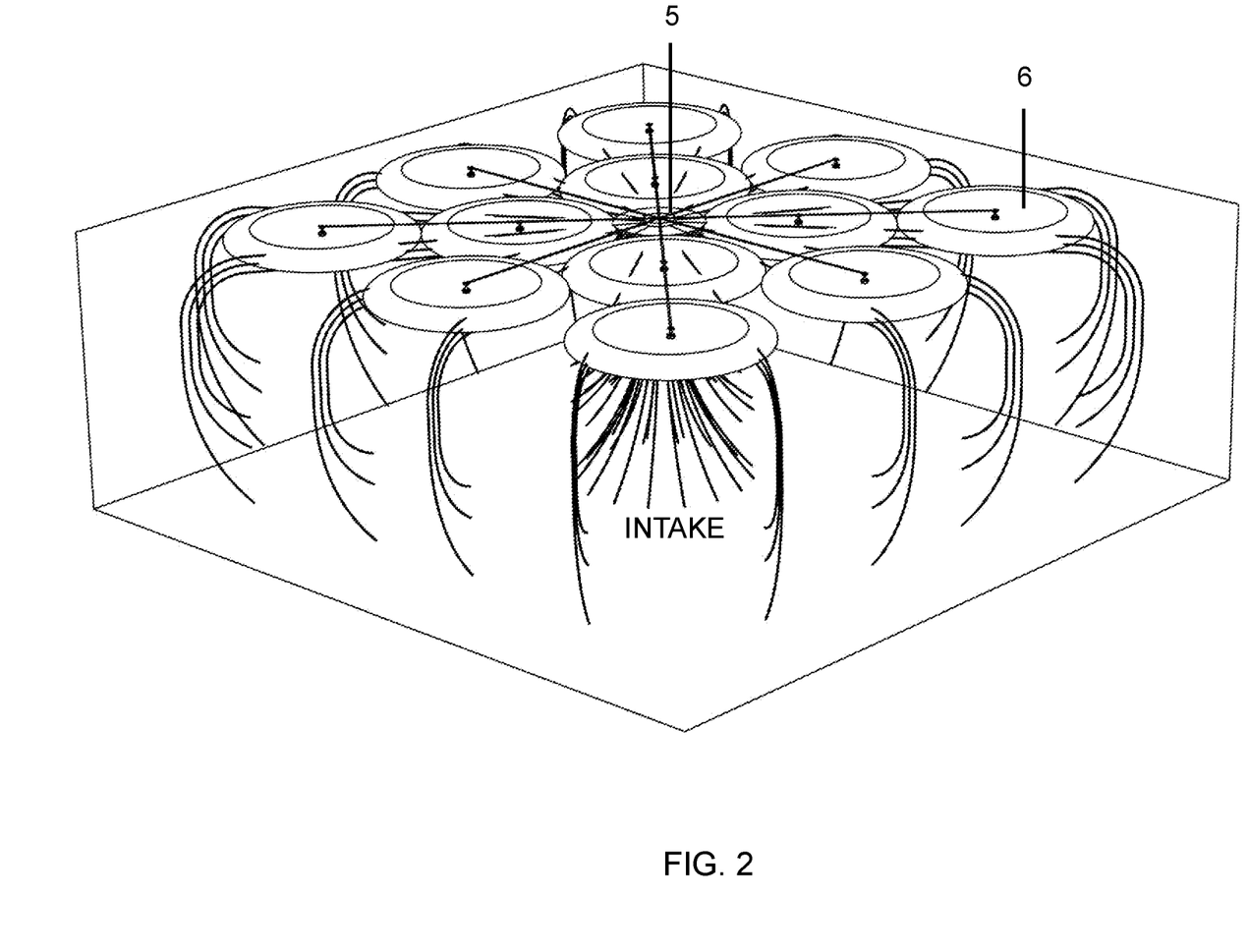
FIG. 2 shows a series of ceiling-mounted emitters positioned around a central air circulation device.

FIG. 2 illustrates an upper air disinfection device where a central air circulator based on the tesla turbine 5 draws in air from the room and exhausts it along the ceiling where it passes through the output of a series of upper air emitters 6. Said emitters are wired to a central location where a DC power supply is present.

Figure 3:
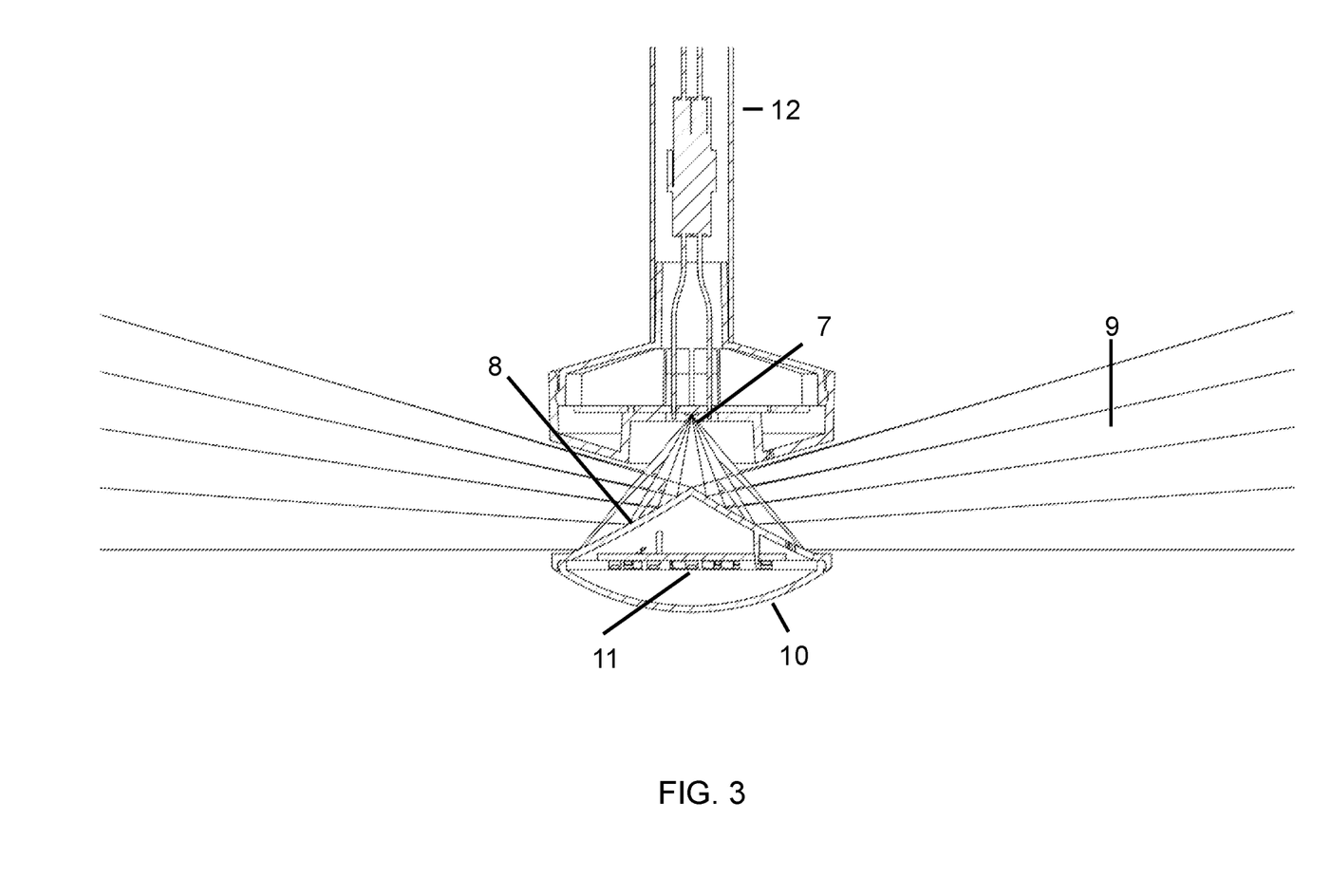
FIG. 3 illustrates an embodiment of an emitter in which light projected from a concentrated source may interact with an axially symmetric reflector and exit the fixture in a substantially horizontal orientation with a controller vertical spread.

FIG. 3 shows a section view of an upper air emitter where a concentrated germicidal light source 7 projects light vertically towards an axially symmetric reflector 8. The surface of said reflector 8 is such that there is a high specular reflection and light rays incident on said reflector 8 will reflect at an angle that is equal to the angle of incidence. The shape of said reflector 8 and position relative to said germicidal light source 7 is such that the reflected rays 9 will be substantially horizontal with a controlled vertical spread a shown. In some embodiments said reflector 8 may be produced from aluminum with a polished finish whereas in other embodiments a thin film may be applied to a substrate such as plastic. Also show in is a surface 10 which is semi translucent, and a series of visible light emitting diodes 11 such that the bottom surface of said emitter is illuminated a visible color for alerting room occupants. In the embodiment illustrated, the emitter shown is hanging from a ceiling and supported by a pole 12, whereas in other embodiments, the support structure and wiring may be introduced from the bottom. In some embodiments multiple instances of reflectors and concentrated light source may be placed vertically adjacently. In some embodiments a concentrated visible light source may be collocated with said germicidal light source 7, such that the germicidal output pattern may be observed by the human eye.

Figure 4:
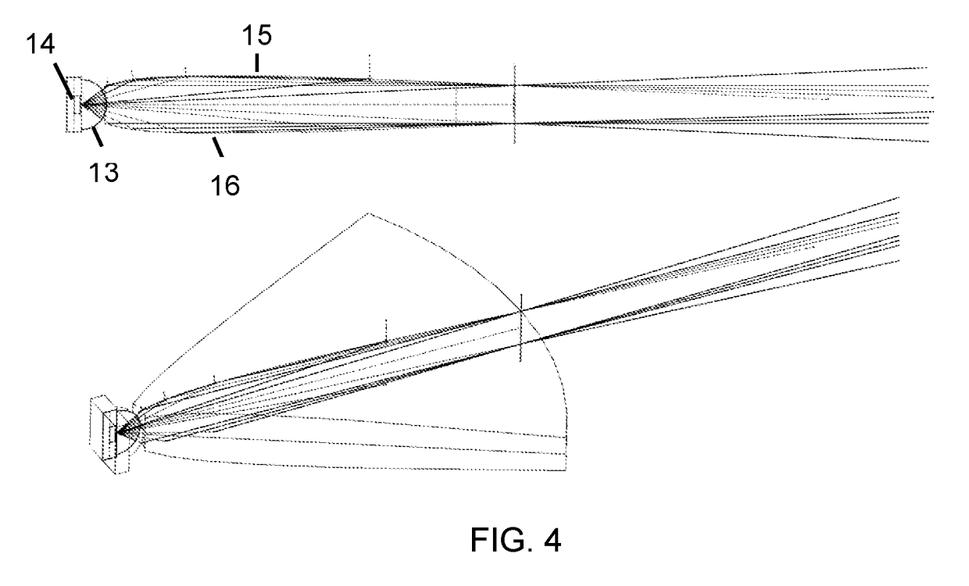
FIG. 4 illustrates an embodiment of an emitter in which a quartz lens reduces the field of view of the LED to a full-width-half-maximum (FWHM) angle of approximately 70 degrees. Reflector surfaces positioned above and below the exiting light are capable of focusing the output in the vertical direction while allowing the horizontal spread to remain at that existing the LED lens.

FIG. 4 illustrates an embodiment of an emitter in which a quartz lens 13 reduces the field of view of an LED 14 to a full-width-half-maximum (FWHM) angle between 40 and 90 degrees, preferably 70 degrees degrees. Reflector surfaces positioned above 15 and below 16 are capable of focusing the output in the vertical direction while allowing the horizontal spread to remain at that emitted from the LED lens. Said reflector surfaces 15, 16 have a complex shape which requires that they be formed from polished aluminum or similarly reflective metal or applied as a thin film coating to a substrate using a film deposition process such as photo-vapor-deposition.

Figure 5:
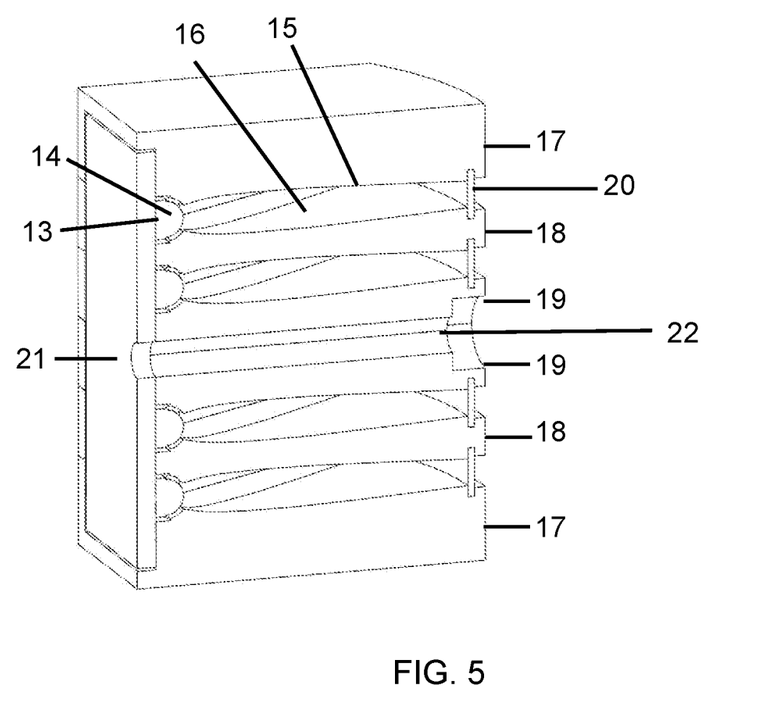
FIG. 5 shows a section view of an embodiment where four instances of the reflector/lens design shown in FIG. 4 are integrated into a single module using a low number of unique parts. Further the inclusion of a series of quartz windows on the output of the optical assembly is shown to mitigate dust intrusion.

FIG. 5 shows a section view of an embodiment where four instances of the reflector/lens design shown in FIG. 4 are integrated into a module using a low number of unique parts. A first part 17 is used in two positions, while a second part 18 is also used in two positions, while a third part 19 is used in two positions as well. Said parts are bonded together whereby they trap four instances of an arc section of quartz 20. Said quartz windows 20 on the output of the optical assembly mitigate dust intrusion. In some embodiments parts 17, 18, and 19 are produced from injection molded plastic and the reflector surfaces are applied as preformed parts or applied as a thin film. The quartz lenses 13 are mounted directly to the LED die packages 14, which are mounted and electrically connected to a printed circuit board 21, preferably made with an aluminum core for the purposes of transferring heat. A passage way 22 is integrated in the module in order to allow a mechanical fastener to register the module to a mounting structure and apply a compressive force to the back side of said printed circuit board 21 such that efficient heat transfer may be achieved.

Figure 6:
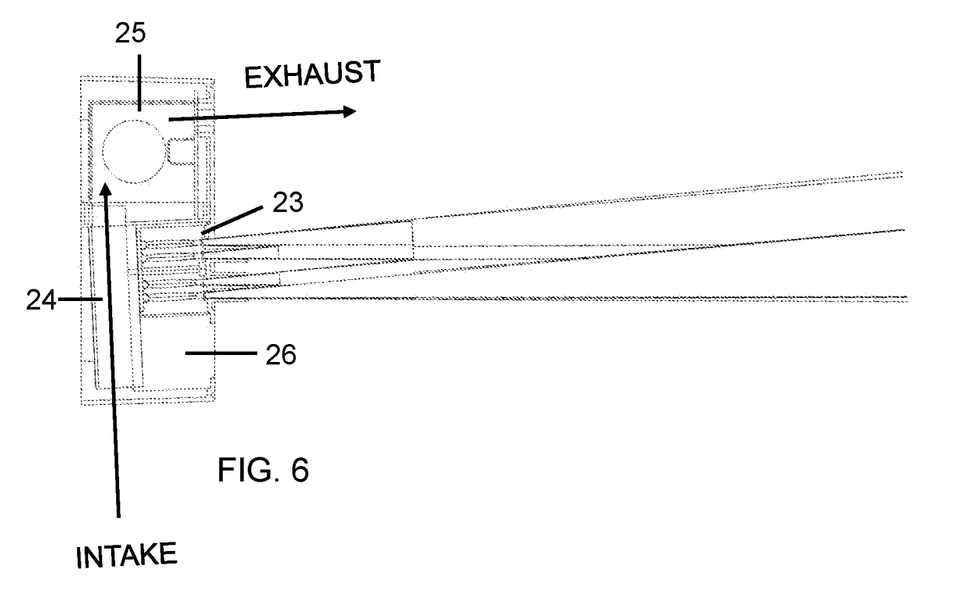
FIG. 6 shows section view of an emitter where the modules shown in FIG. 5 are mounted to a finned heat sink while a cross flow blower draws room air over said heat sink and exhausts in order to promote air mixing and transfer heat from LED modules into said air stream.

FIG. 6 shows a section view of an emitter where the module 23 shown in FIG. 5 are mounted to a finned heat sink 24 while a cross flow blower 25 draws room air over said heat sink 26 and exhausts it in order to promote air mixing and transfer heat from LED modules into said air stream. Said modules 23 are connected to said heat sink 24 with a mechanical fastener 25 capable of applying a compressive load to ensure efficient heat transfer. Additionally, interconnects embedded in said heat sink 24 make electrical connection with electrodes on said printed circuit boards 21 as well as a printed circuit board contained in a control module 26 located adjacent to said modules 23.

Figure 7:
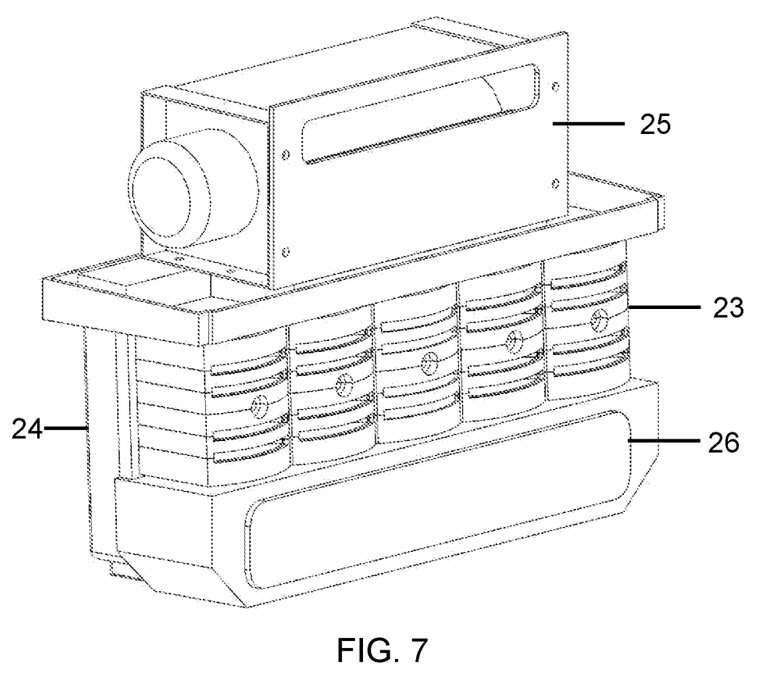
FIG. 7 illustrates the emitter shown in FIG. 6 in isometric view. It shows a series of the modules illustrated in FIG. 5 mounted to said heat sink. Additionally, it shows a window and volume for a system controller which may contain a means for communicating with a wireless network, as well as environmental and occupancy sensors.

FIG. 7 illustrates and isometric view of the emitter shown in FIG. 6. It shows a series of the modules 23 illustrated in FIG. 5 mounted to said heat sink 24. Additionally, it shows a window and volume for a system controller 26 which may contain a means for communicating with a wireless network, as well as environmental and occupany sensors.

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not to be limited to the details given herein, but may be modified within the scope and equivalents of the disclosed embodiments and/or any of the claims included herein.

While some preferred materials are described in this invention, the invention is not limited to these materials. Some other materials that may be used in the construction of an upper-room disinfection device and system of use include but are not limited to: plastics, rubbers, wood and other organic materials, metal alloys, composite materials and structures, and foams. Similarly, while specific manufacturing techniques are described in the invention, the invention is not limited to these methods. Some methods that may be used in the construction of an upper-room disinfection device and system of use include but are not limited to: injection molding, spin forming, polishing, vacuum deposition, sand casting, dies casting, stamping, laser cutting, water-jet cutting, powder-coating, painting, anodizing, extrusion, machining, forming, swaging, welding, and/or bonding.

It will be appreciated that a number of variations can be made to the architecture, relationships, and examples presented in connection with figures and/or associated description within the scope of the inventive body of work. For example, certain illustrated processing steps may not be included in the data processing workflow and/or additional processing steps may be included. Thus, it will be appreciated that the architecture, relationships, and examples presented in connection with the figures and/or associated description are provided for purposes of illustration and explanation, and not limitation.

What is claimed is:

1. An upper-air disinfection device, comprising:
 (a) one or more upper-air emitters outputting horizontally oriented germicidal light, positioned above the heads of room occupants at about 7 feet or higher, wherein each emitter is mounted to the wall or ceiling at regularly spaced intervals, wherein each emitter is powered by a power source supplying between 9V DC and 48V DC electricity,
(b) one or more power supplies converting main AC electricity into DC voltage,
(c) a series of wires connecting said emitters and said power supplies, and
(d) one or more centralized air circulators for inducing airflow through said germicidal light,
whereby germicidal light can be distributed into the upper room of a space.

2. An upper-air disinfection device as in claim 1, further comprising one or more control modules capable of communicating with a wireless network.

3. An upper-air disinfection device, comprising:
(a) one or more upper-air emitters outputting horizontally oriented germicidal light, positioned above the heads of room occupants at about 7 feet or higher, wherein each emitter is mounted to the wall or ceiling at regularly spaced intervals, wherein each emitter is powered by a power source supplying between 9V DC and 48V DC electricity,
(b) one or more power supplies converting main AC electricity into DC voltage,
(c) a series of wires connecting said emitters and said power supplies, and
(d) one or more sensors capable of detecting CO2 concentrations at various locations within a space.

4. An upper-air disinfection device as in claim 1, further comprising one or more sensors capable of detecting when a human has entered the space where said germicidal light is projected.

5. An upper-air disinfection device, comprising:
(a) one or more upper-air emitters outputting horizontally oriented germicidal light, positioned above the heads of room occupants at about 7 feet or higher, wherein each emitter is mounted to the wall or ceiling at regularly spaced intervals, wherein each emitter is powered by a power source supplying between 9V DC and 48V DC electricity, wherein one or more of said emitters has a surface visible to room occupants which illuminates when germicidal light is being projected
(b) one or more power supplies converting main AC electricity into DC voltage, and
(c) a series of wires connecting said emitters and said power supplies,
whereby germicidal light can be distributed into the upper room of a space.

6. An upper-air disinfection device as in claim 1, wherein one or more of said emitters has the capability to track the time that each light source has been powered.

7. An upper-air disinfection device as in claim 1, further comprising one or more sound generation devices capable of emitting a noise intended to communicate the effect of inactivation.

8. An upper-air disinfection emitter, comprising:
(a) a concentrated light source producing germicidal light where the volume of the light producing material is less than 200 cubic millimeters, projecting vertically, and
(b) an axially symmetric reflector positioned below said light source, wherein said reflector's surface has a specular reflection of greater than 70% of said germicidal light incident on said reflector,
whereby the projected light will be reflected into a horizontally oriented pattern.

9. An upper-air disinfection emitter, comprising:
(a) a concentrated light source producing germicidal light where the volume of the light producing material is less than 200 cubic millimeters, projecting vertically, and
(b) an axially symmetric reflector positioned below said light source, wherein said reflector's profile and position is controlled to achieve a desired vertical divergence of said horizontally projected light between zero and ten degrees,
whereby the projected light will be reflected into a horizontally oriented pattern.

10. An upper-air disinfection emitter, comprising:
(a) a concentrated light source producing germicidal light where the volume of the light producing material is less than 200 cubic millimeters, projecting vertically, wherein said germicidal light source is a krypton-chloride excimer lamp, and
(b) an axially symmetric reflector positioned below said light source,
whereby the projected light will be reflected into a horizontally oriented pattern.

11. An upper-air disinfection emitter as in claim 8, wherein said germicidal light source is a one or more light-emitting-diodes.

12. An upper-air disinfection emitter, comprising:
(a) a concentrated light source producing germicidal light where the volume of the light producing material is less than 200 cubic millimeters, projecting vertically,
(b) an axially symmetric reflector positioned below said light source, and
(c) a light source producing visible light positioned alongside said germicidal light source, whereby the output pattern of said emitter may be observed with the human eye,
whereby the projected light will be reflected into a horizontally oriented pattern.

13. An upper-air disinfection emitter, comprising:
(a) a concentrated light source producing germicidal light where the volume of the light producing material is less than 200 cubic millimeters, projecting vertically, wherein said reflector is fabricated from polished aluminum, and
(b) an axially symmetric reflector positioned below said light source,
whereby the projected light will be reflected into a horizontally oriented pattern.

14. An upper-air disinfection emitter as in claim 8, wherein said reflector is comprised of a substrate coated by a thin film of reflective material.

15. An upper-air disinfection emitter, comprising:
(a) one or more light emitting diodes (LED) producing germicidal light oriented horizontally,
(b) a focusing optic made of SiO2 (quartz) positioned in front of each said LED, for reducing the full width half maximum (FWHM) field of view (FOV) of the output beam from said optic to 80 degrees or less, and
(c) a set of reflectors positioned above and below output of each said optic, reducing the vertical beam divergence to 10 degrees or less.

16. An upper-air disinfection emitter as in claim 15, further comprising a cross-flow tangential air circulator inducing the flow of air into said beam outputs.

17. An upper-air disinfection emitter as in claim 16, further comprising a finned heat sink wherein the airflow from said air circulator passes through said finned heat sink to which said LEDs are thermally connected, whereby the heat produced by the LEDs is transferred to the circulator airflow.

18. An upper-air disinfection emitter as in claim 15, further comprising a light sources producing visible light positioned alongside said germicidal light source, whereby the output pattern of said emitter may be observed with the human eye.

19. An upper-air disinfection emitter as in claim 8, further comprising a light source producing visible light positioned alongside said germicidal light source, whereby the output pattern of said emitter may be observed with the human eye.

20. An upper-air disinfection emitter as in claim 8, wherein said germicidal light source is a krypton-chloride excimer lamp.

\* \* \* \* \*